(12) United States Patent
Tanaka et al.

(10) Patent No.: US 11,363,940 B2
(45) Date of Patent: Jun. 21, 2022

(54) ENDOSCOPE

(71) Applicant: FUJIFILM Corporation, Tokyo (JP)

(72) Inventors: Koichi Tanaka, Kanagawa (JP); Takeshi Yukiiri, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 360 days.

(21) Appl. No.: 16/120,318

(22) Filed: Sep. 3, 2018

(65) Prior Publication Data

US 2019/0090723 A1 Mar. 28, 2019

(30) Foreign Application Priority Data

Sep. 22, 2017 (JP) .............................. JP2017-182927

(51) Int. Cl.
*A61B 1/00* (2006.01)
*A61B 1/12* (2006.01)

(52) U.S. Cl.
CPC ........ *A61B 1/00091* (2013.01); *A61B 1/0008* (2013.01); *A61B 1/00094* (2013.01); *A61B 1/00096* (2013.01); *A61B 1/126* (2013.01)

(58) Field of Classification Search
CPC . A61B 1/00091; A61B 1/00096; A61B 1/126; A61B 1/000163; A61B 1/00165; A61B 1/000167; A61B 1/0017; A61B 1/00172; A61B 1/00174; A61B 1/00177; A61B 1/00179; A61B 1/00181; A61B 1/00183; A61B 1/00186; A61B 1/00188;

(Continued)

(56) References Cited

U.S. PATENT DOCUMENTS 5,518,502 A * 5/1996 Kaplan .................. A61B 1/127
  600/156
5,630,795 A * 5/1997 Kuramoto .......... A61B 1/00137
  604/35

(Continued)

FOREIGN PATENT DOCUMENTS

CN  101098655  1/2008
CN  101472517  7/2009

(Continued)

OTHER PUBLICATIONS

"Search Report of Europe Counterpart Application", dated Jan. 15, 2019, p. 1-p. 25.

(Continued)

*Primary Examiner* — Ryan N Henderson
(74) *Attorney, Agent, or Firm* — JCIPRNET (57) ABSTRACT

An endoscope of the invention has a first surface constituting a distal end surface of the insertion part, a second surface formed on a projecting part projecting from the first surface to a front side, and an observation window provided on the second surface. The first surface has a fluid jetting nozzle, a first protective projection, and a second protective projection. The projecting part has an extending part extending from the observation window toward a side opposite to the fluid jetting nozzle. In all combinations of imaginary planes capable of coming into contact with, from the front side, at least two of the fluid jetting nozzle, the first protective projection, the second protective projection, and the extending part, the imaginary planes are disposed forward of the observation window.

12 Claims, 11 Drawing Sheets

(58) Field of Classification Search
CPC .............. A61B 1/0019; A61B 1/00193; A61B 1/00195; A61B 1/00197; A61B 1/002; A61B 1/04; A61B 1/042; A61B 1/043; A61B 1/05; A61B 1/051; A61B 1/055; A61B 1/06; A61B 1/0607; A61B 1/0615; A61B 1/0623; A61B 1/063; A61B 1/0638; A61B 1/0646; A61B 1/0653; A61B 1/0661; A61B 1/0669; A61B 1/0676; A61B 1/0684; A61B 1/07; A61B 1/12; A61B 1/127; A61B 1/0008; A61B 1/00094; A61B 1/015; G02B 23/2476
See application file for complete search history.

(56) References Cited

U.S. PATENT DOCUMENTS

| | | | | |
|---|---|---|---|---|
| 5,685,823 | A * | 11/1997 | Ito | A61B 1/00091 |
| | | | | 600/121 |
| 7,896,802 | B2 * | 3/2011 | Otawara | G01N 21/6456 |
| | | | | 600/176 |
| 7,936,369 | B2 | 5/2011 | Takase et al. | |
| 8,033,990 | B2 * | 10/2011 | Otawara | G02B 23/2423 |
| | | | | 600/129 |
| 8,092,375 | B2 * | 1/2012 | Otawara | A61B 1/043 |
| | | | | 600/176 |
| 8,394,013 | B2 * | 3/2013 | Ichimura | A61B 1/0623 |
| | | | | 600/129 |
| 8,419,631 | B2 * | 4/2013 | Kase | G02B 23/2476 |
| | | | | 600/129 |
| 8,740,779 | B2 * | 6/2014 | Yoshida | A61B 1/0638 |
| | | | | 600/177 |
| 8,777,845 | B2 * | 7/2014 | Ikeda | A61B 1/127 |
| | | | | 600/129 |
| 9,173,555 | B2 * | 11/2015 | Ikeda | A61B 1/00096 |
| 9,282,882 | B2 * | 3/2016 | Ikeda | A61B 1/018 |
| 9,943,217 | B2 * | 4/2018 | Ikeda | A61B 1/00163 |
| 10,779,717 | B2 * | 9/2020 | Kuwae | A61B 1/00091 |
| 2006/0161047 | A1 * | 7/2006 | Miyoshi | A61B 1/00091 |
| | | | | 600/173 |
| 2006/0229497 | A1 * | 10/2006 | Toyama | A61B 1/00091 |
| | | | | 600/156 |
| 2007/0027360 | A1 * | 2/2007 | Mitsuya | A61B 1/00071 |
| | | | | 600/141 |
| 2007/0260118 | A1 * | 11/2007 | Otawara | A61B 1/00096 |
| | | | | 600/176 |
| 2008/0064928 | A1 * | 3/2008 | Otawara | H04N 5/2251 |
| | | | | 600/129 |
| 2008/0086032 | A1 * | 4/2008 | Ichimura | A61B 1/05 |
| | | | | 600/156 |
| 2009/0093681 | A1 * | 4/2009 | Ichimura | A61B 1/00096 |
| | | | | 600/178 |
| 2011/0306838 | A1 * | 12/2011 | Ikeda | A61B 1/00091 |
| | | | | 600/157 |
| 2012/0226104 | A1 * | 9/2012 | Ikeda | A61B 1/127 |
| | | | | 600/129 |
| 2014/0058204 | A1 | 2/2014 | Ikeda et al. | |
| 2014/0094659 | A1 * | 4/2014 | Hamazaki | G02B 23/2476 |
| | | | | 600/157 |
| 2017/0049308 | A1 | 2/2017 | Ikeda et al. | |
| 2020/0000330 | A1 | 1/2020 | Ikeda et al. | |

FOREIGN PATENT DOCUMENTS

| | | | |
|---|---|---|---|
| CN | 102273997 | 12/2011 | |
| CN | 102648841 | 8/2012 | |
| CN | 102652663 | 9/2012 | |
| EP | 2491848 | 8/2012 | |
| EP | 2494909 | 9/2012 | |
| EP | 2494909 A1 * | 9/2012 | ............... A61B 1/07 |
| JP | 2005192638 | 7/2005 | |
| JP | 2009279291 | 12/2009 | |
| JP | 2009279291 A * | 12/2009 | |
| JP | 2010200944 | 9/2010 | |
| JP | 2011206229 | 10/2011 | |
| JP | 2012179078 | 9/2012 | |
| JP | 2012179221 | 9/2012 | |
| JP | 2015136514 A * | 7/2015 | |

OTHER PUBLICATIONS

"Office Action of Japan Counterpart Application", dated Aug. 21, 2020, with English translation thereof, p. 1-p. 6.

"Office Action of China Counterpart Application" with English translation thereof, dated Dec. 28, 2021, p. 1-p. 14.

* cited by examiner

ENDOSCOPE

CROSS-REFERENCE TO RELATED APPLICATIONS

The present application claims priority under 35 U.S.C. § 119 to Japanese Patent Application No. 2017-182927, filed on Sep. 22, 2017. Each of the above application(s) is hereby expressly incorporated by reference, in its entirety, into the present application.

BACKGROUND OF THE INVENTION

1. Field of the Invention

The present invention relates to an endoscope, and particularly, to an endoscope for improving protection of an observation window in a distal end part of an insertion part.

2. Description of the Related Art

For example, reduction in diameter of the insertion part is required in an upper endoscope, such as a gastroscope. In a distal end part of an insertion part of such an endoscope, an observation window that takes in subject light from an area to be observed, and an illumination window that emits illumination light to the area to be observed are disposed on a distal end surface. Additionally, in order to remove adhering substances, such as a body fluid adhering to the observation window, a fluid jetting nozzle (air/water supply nozzle), which jets a fluid, such as a cleaning liquid (water or the like) or gas (air or the like), toward the observation window, is disposed in the distal end surface.

In a case where the distal end surface of the endoscope comes into contact with a top plate of a workbench at the time of preparatory work, a floor surface at the time of being gripped by an operator at the time of examination, a floor surface at the time of being hung on a hanger, baths of a sink and a washer at the time of cleaning and disinfection, or the like (hereinafter referred to as a "contacted member"), there is a concern that the observation window and the illumination window may be damaged by coming into contact with the above top plate, floor surfaces, and baths. Particularly, in a case where the observation window (objective lens) has a convex shape, a possibility of contact with the observation window becomes high.

As an endoscope that prevents contact with a lens portion of the observation window and improves shock resistance, for example, the following JP2005-192638 discloses an endoscope in which a first contact distal end part provided in an air/water supply nozzle and a second contact end part provided except for at least one of the observation window or illumination means are formed.

SUMMARY OF THE INVENTION

However, the endoscope described in JP2005-192638 is adapted such that the first contact distal end part and the second contact distal end part prevent the endoscope from contacting with the contacted member. However, in a case where the first contact end part and the second contact end part are laterally shifted from a straight line connecting these contact end parts, there is a case where a contacted member, such as a top surface or a floor, may come into contact with the observation window.

The invention has been made in view of such circumstances, and an object thereof is to provide an endoscope that can prevent contact with an observation window against contact from all directions.

In order to achieve the object of the invention, an endoscope related to the invention comprises an insertion part to be inserted into a subject; a first surface that constitutes a distal end surface of the insertion part; a second surface that is formed on a projecting part projecting from the first surface to a front side; an observation window that is provided on the second surface to observe an inside of the subject; a nozzle that is provided on the first surface to jet a fluid toward the observation window; a first protective projection that is provided on the first surface and is disposed on one side of an imaginary straight line connecting a center of the observation window and a center of the nozzle; a second protective projection that is provided on the first surface and is disposed on the other side of the imaginary straight line; and an extending part that is provided on the projecting part and extends from the observation window toward a side opposite to the nozzle. In all combinations of imaginary planes capable of coming into contact with at least two of the nozzle, the first protective projection, the second protective projection, and the extending part from the front side, the imaginary planes are disposed forward of the observation window.

In the one aspect of the invention, it is preferable that the first protective projection and the second protective projection are provided to project forward of the observation window.

In the one aspect of the invention, it is preferable that the nozzle is provided to project forward of the first protective projection and the second protective projection.

In the one aspect of the invention, it is preferable that the observation window is provided to project forward of the extending part.

In the one aspect of the invention, it is preferable that the endoscope further comprises a first illumination window that is provided on the first surface and is disposed between the observation window and the first protective projection; and a second illumination window that is provided on the first surface and is disposed between the observation window and the second protective projection.

In the one aspect of the invention, it is preferable that at least one of the first protective projection or the second protective projection is disposed at a position adjacent to an illumination window disposed on the same side of the imaginary straight line.

In the one aspect of the invention, it is preferable that the first protective projection and the second protective projection are provided along an outer edge of the first surface.

In the one aspect of the invention, it is preferable that the first protective projection and the second protective projection are disposed outside an endoscope observation visual field range.

In the one aspect of the invention, it is preferable that the first protective projection and the second protective projection are disposed outside a visual field range of the observation window.

In the one aspect of the invention, it is preferable that the extending part is disposed outside an endoscope observation visual field range.

In the one aspect of the invention, it is preferable that the extending part is disposed outside a visual field range of the observation window.

According to the invention, the nozzle, the extending part extending from the observation window toward the side opposite to the nozzle, and the first protective projection and the second protective projection on both sides of the imaginary straight line connecting the center of the observation window and the center of the nozzle are provided, and the nozzle, the extending part, the first protective projection, and the second protective projection can prevent a contacted member from coming into contact with the observation window. Hence, the observation window can be protected from the contacted member.

DESCRIPTION OF THE PREFERRED EMBODIMENTS

Hereinafter, preferable embodiments of an endoscope related to the invention will be described according to the accompanying drawings.

Figure 1:
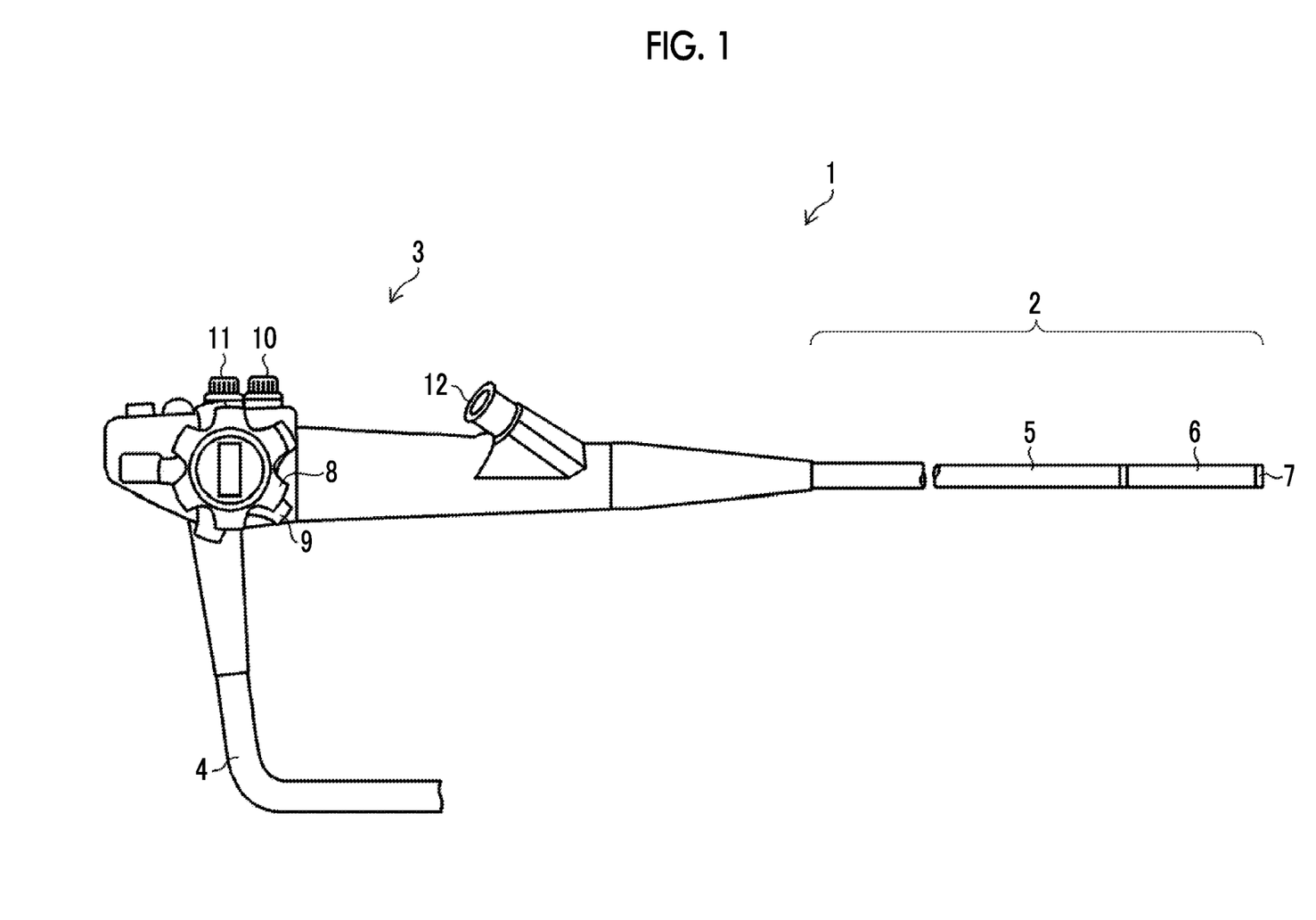
FIG. 1 is an overall view of an endoscope to which the invention is applied.

FIG. 1 is a configuration view illustrating an endoscope 1 related to an embodiment of the invention. An endoscope 1 in this drawing includes an insertion part 2 inserted into a patient's body, an operating part 3 provided continuously with a proximal end of the insertion part 2 and used for gripping the endoscope 1, operating the insertion part 2, and the like, and a universal cord 4 connected the endoscope 1 to system constituent devices, such as a light source device (not illustrated) and a processor device. The endoscope 1 of the present embodiment is a gastroscope.

The insertion part 2 has a distal end, a proximal end and a longitudinal axis, and is constituted of a flexible part 5, a bending part 6, and a distal end part 7 that are sequentially and continuously provided from the proximal end toward a distal end. The flexible part 5 has flexibility and bends in arbitrary directions along an insertion path of the insertion part 2. The bending part 6 bends in upward, downward, rightward, and leftward directions through the operation of angle knobs 8 and 9 of the operating part 3. The distal end part 7 includes an illumination unit or the like that irradiates an observation unit for imaging an observation area in a living body or an area to be observed with illumination light.

Figure 2:
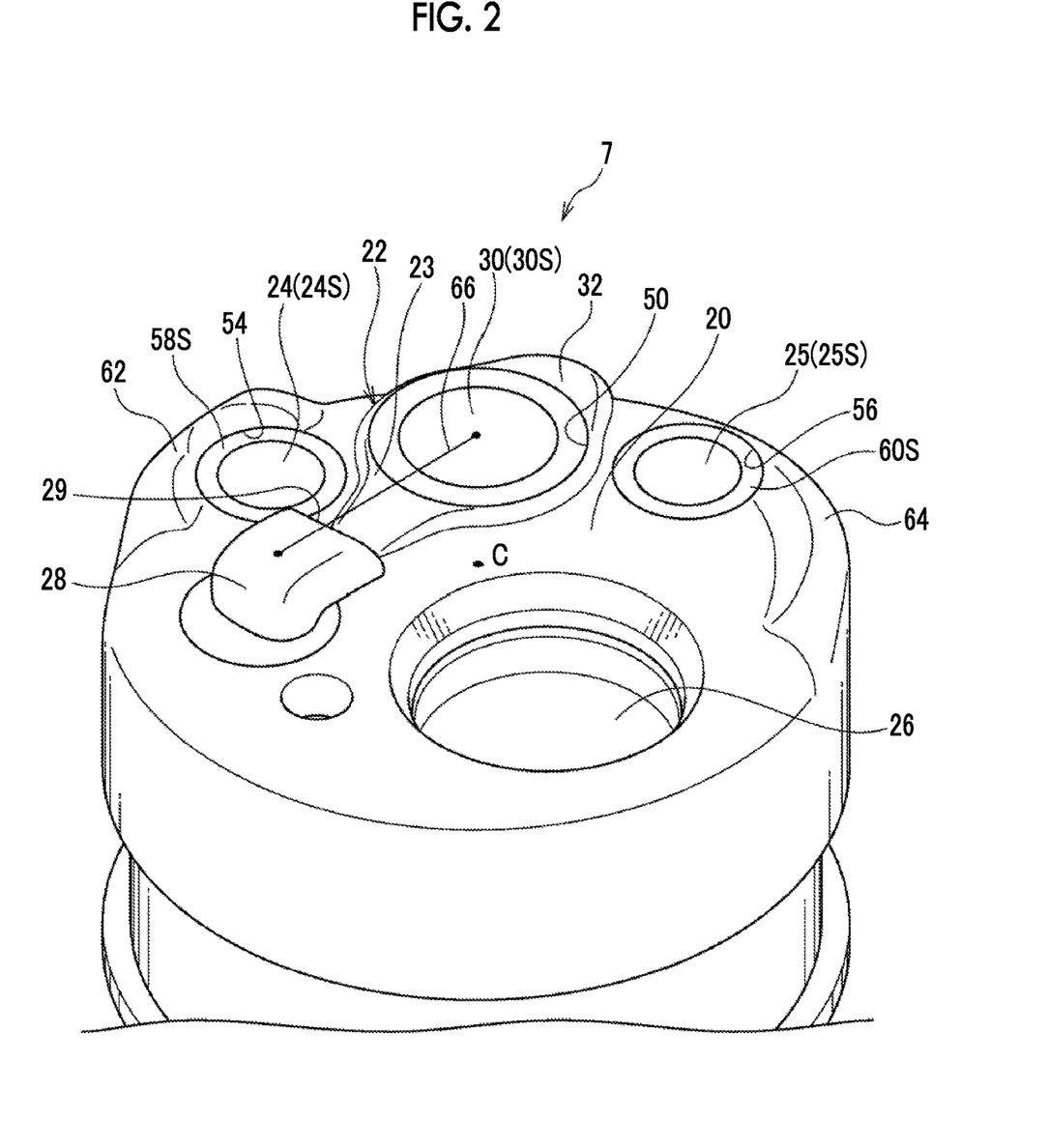
FIG. 2 is a perspective view of a distal end surface of the endoscope.
Figure 3:
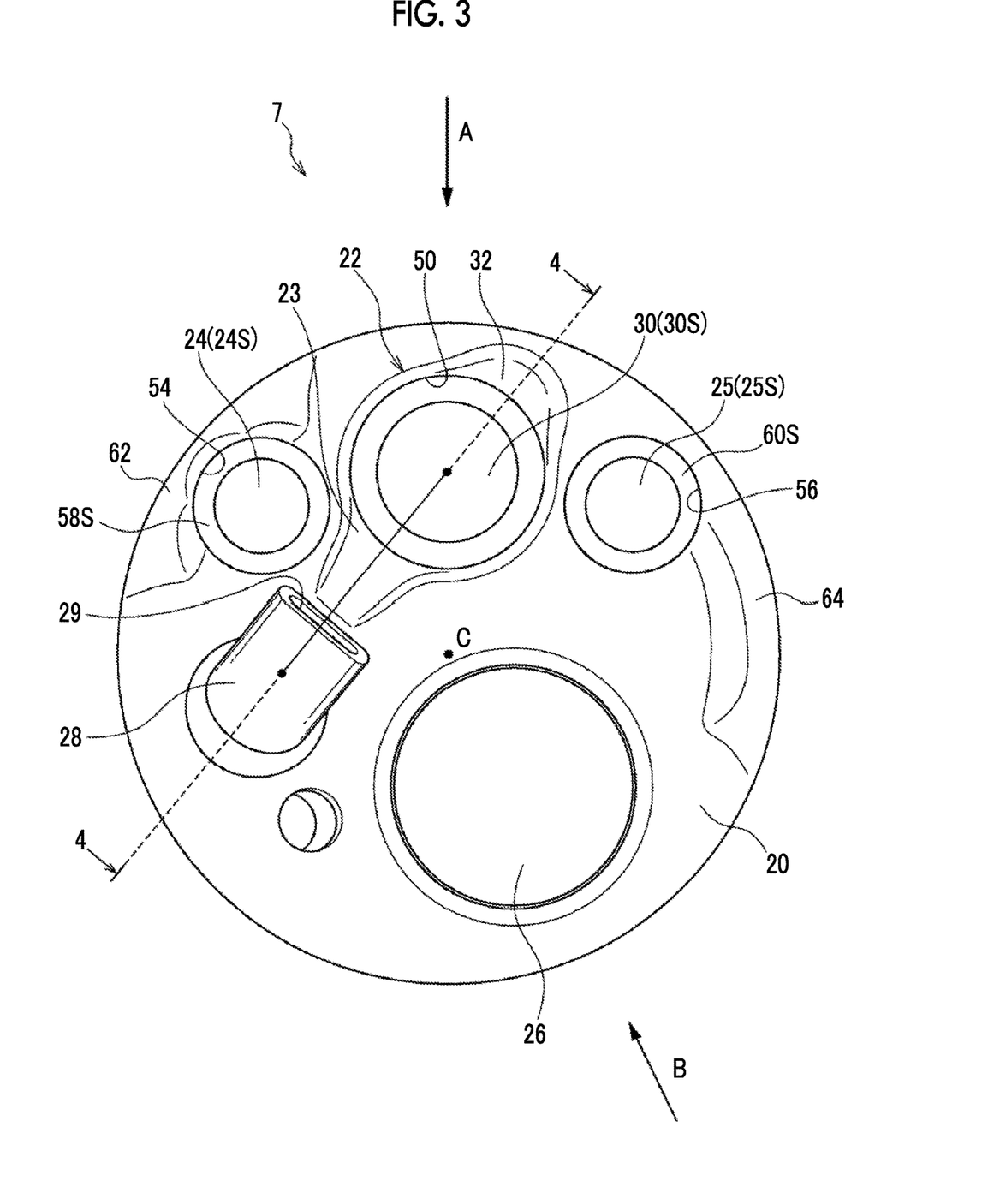
FIG. 3 is a plan view of the distal end surface of the endoscope.

FIG. 2 is a perspective view illustrating the distal end part 7 in an enlarged manner, and FIG. 3 is a plan view. As illustrated in FIGS. 2 and 3, the distal end part 7 is provided with a first surface 20 that constitutes a distal end surface along a plane substantially perpendicular to the longitudinal axis that is an axis of the insertion part 2. The first surface 20 has a projecting part 22 projecting from the first surface 20 to a front side, and a second surface 23 is formed in the projecting part 22. The first surface 20 has a first illumination window 24, a second illumination window 25, a treatment tool outlet 26, and a fluid jetting nozzle 28, and the like. Additionally, the second surface 23 has an observation window 30 for observing the inside of a subject. In addition, in the following, simply the term "longitudinal axis" indicates the longitudinal axis of the insertion part 2. Additionally, the "front side" means a distal end side of the longitudinal axis of the insertion part 2 and means an affected area side in a case where the endoscope 1 is inserted into a patient.

The observation window 30 is a constituent element of the observation unit that acquires an image of an area to be observed and takes subject light from the area to be observed into an optical system (an imaging lens and the like), which is another constituent element of the observation unit, and imaging means. The image captured by the observation unit is sent to the processor device connected by the universal cord 4 as an observation image (endoscopic image).

The first illumination window 24 and the second illumination window 25 are constituent elements of the illumination unit to be mounted on the distal end part 7, and irradiate the area to be observed with illumination light emitted from a light emitting part that is another constituent element of the illumination unit. The illumination light emitted from the light emitting part is propagated through a light guide inserted through the endoscope 1 from the light source device connected by the universal cord 4.

A treatment tool outlet 26 communicates with a treatment tool inlet 12 (refer to FIG. 1) of the operating part 3 through a treatment tool insertion channel inserted through the insertion part 2, and a treatment tool inserted from the treatment tool inlet 12 is delivered from the treatment tool outlet.

Additionally, a suction channel is coupled to the treatment tool insertion channel, and suction from the treatment tool outlet 26 is performed by the operation of a suction button 11 (refer to FIG. 1) of the operating part 3.

The fluid jetting nozzle 28 has a jetting nozzle 29, which is an opening that jets a fluid, disposed toward the observation window 30 and jets a cleaning liquid or gas to a surface 30S of the observation window 30 and a peripheral part thereof.

The fluid jetting nozzle 28 communicates with an air/water supply channel inserted through the endoscope 1, and is connected to an air/water supply device (not illustrated) connected to the universal cord 4, via the air/water supply channel.

Then, in a case where a leakage hole formed in an air/water supply button 10 (refer to FIG. 1) of the operating part 3 is closed by a finger, the gas from the air/water supply device is jetted from the fluid jetting nozzle 28, and in a case where the air/water supply button 10 is pushed with the finger that has closed the leakage hole, the cleaning liquid from the air/water supply device is jetted from the fluid jetting nozzle 28.

In addition, as a procedure of cleaning the observation window 30, for example, after the cleaning liquid is jetted from the fluid jetting nozzle 28 to remove adhering substances, such as blood and a body fluid, which have adhered to the observation window 30, the gas is jetted from the fluid jetting nozzle 28 to remove the cleaning liquid remaining on the observation window 30 or a region adjacent thereto.

The projecting part 22 has an extending part 32 extending from the observation window 30 toward a side opposite to the fluid jetting nozzle 28. The extending part 32 is provided to extend parallel to a direction perpendicular to the longitudinal axis from the second surface 23, and the surface of the extending part 32 is formed flush with the second surface 23.

As illustrated in FIG. 3, the distal end surface of the distal end part 7 is constituted of the first surface 20 substantially perpendicular to the longitudinal axis of the insertion part 2, and a second surface 23 formed in the projecting part 22 projecting from the first surface 20 to the front side. The distal end surface is formed on the basis of a circular flat surface having an intersection position with the longitudinal axis as a center C (hereinafter referred to as the center C of the distal end surface).

Also, the first illumination window 24, the second illumination window 25, the treatment tool outlet 26 that is an opening formed in the distal end part body 40, the fluid jetting nozzle 28, a first protective projection 62, and a second protective projection 64 are disposed on the first surface 20. The observation window 30 is disposed on the second surface 23.

As illustrated in FIG. 3, as a planar arrangement relationship of the respective parts, the surface 30S of the observation window 30 is disposed at a position biased to a peripheral edge of the distal end surface with respect to the center C of the distal end surface. The fluid jetting nozzle 28 is disposed such that the jetting nozzle 29 faces the observation window 30 side. Additionally, the first illumination window 24 and the second illumination window 25 are disposed at positions substantially opposite to each other with the observation window 30 interposed therebetween. The treatment tool outlet 26 is disposed at a remaining space where the observation window 30, the fluid jetting nozzle 28, the first illumination window 24, and the second illumination window 25 are not disposed. Moreover, the first protective projection 62 and the second protective projection 64 are disposed at an outer edge part of the first surface 20. Specifically, the first protective projection 62 is disposed on one side (setting to FIG. 3 the first illumination window 24 side) of an imaginary straight line 66 connecting the center of the observation window 30 and the center of the fluid jetting nozzle 28, and the second protective projection 64 is disposed on the other side (the second illumination window 25 side in FIG. 3).

The surface 30S of the observation window 30 can be, for example, a convex surface projecting toward the front side, and is disposed at an opening 50 formed in the projecting part 22.

Additionally, a space that communicates with the inside of the distal end part 7 from a gap between a peripheral edge of the surface 30S of the observation window 30 and a peripheral edge of an opening 50 is filled up with an adhesive 52 (refer to FIG. 4), and a surface 52S (refer to FIG. 4) of the adhesive 52 is disposed between the peripheral edge of the surface 30S of the observation window 30 and the peripheral edge of the opening 50.

A surface 24S of the first illumination window 24 and a surface 25S of the second illumination window 25 are respectively formed of, for example, flat surfaces, are disposed perpendicularly to the longitudinal axis of the insertion part 2, and are respectively disposed in openings 54 and 56 formed in the distal end part body 40.

Additionally, surfaces 58S and 60S of adhesives are respectively disposed between a peripheral edge of the surface 24S of the first illumination window 24 and a peripheral edge of an opening 54, and between a peripheral edge of the surface 25S of the second illumination window 25 and a peripheral edge of an opening 56, similar to the above-described surface 52S of the adhesive 52 between the peripheral edge of the surface 30S of the observation window 30 and the peripheral edge of the opening 50, and are disposed flush with the surface 24S of the first illumination window 24 and the surface 25S of the second illumination window 25.

Figure 4:
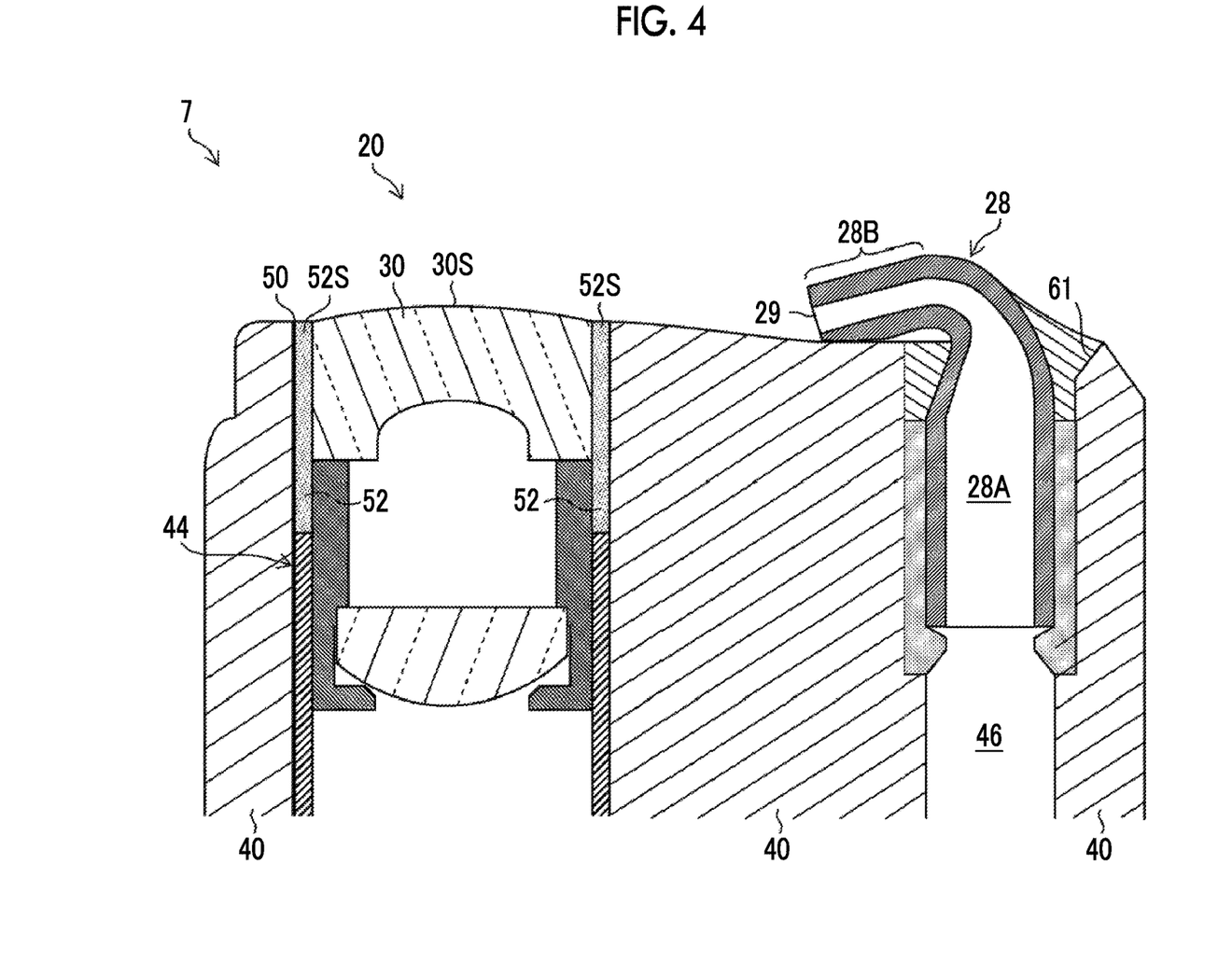
FIG. 4 is a view as seen in the direction of arrow 4-4 of the distal end surface of FIG. 3.

FIG. 4 is a sectional view as seen in the direction of arrow 4-4 of FIG. 3. The distal end part 7 is formed of hard materials, such as metal, and has the distal end part body 40 that holds various components disposed in the distal end part 7.

In addition, in this drawing, a lens barrel 44 that accommodates the observation window 30 and an imaging lens that constitute the observation unit, and an end part of the air/water supply channel 46 connected to the fluid jetting nozzle 28 are illustrated as components held by the distal end part body 40. An optical axis of the observation window 30 (and imaging lens) is substantially parallel to the longitudinal axis of the insertion part 2 in the present embodiment.

The fluid jetting nozzle 28 is disposed such that the shape thereof from a proximal end 28A connected to the end part of the air/water supply channel 46 as illustrated in FIG. 4 to a distal end portion 28B in which the jetting nozzle 29 is formed is L-shaped, and the distal end portion 28B of the fluid jetting nozzle 28 projects from an opening 61 formed in the distal end part body 40 to the distal end side in the direction of the longitudinal axis of the insertion part 2.

Additionally, the jetting nozzle 29 of the fluid jetting nozzle 28 is disposed toward the observation window 30. The jetting nozzle 29 is an oblong opening (plane) substantially perpendicular to an axis of a pipe line of the fluid jetting nozzle 28, and is disposed such that a jetting axis passing through the center of the jetting nozzle 29 faces substantially the center of the surface 30S of the observation window 30 in a front view of the first surface 20 as seen from the direction of the longitudinal axis of the insertion part 2 (refer to FIG. 3).

In addition, a gap between an outer wall surface of the fluid jetting nozzle 28 and a peripheral edge of the opening 61 is sealed and fixed by a sealing member, such as an adhesive.

In the present embodiment, in addition to the above-described configuration, the first surface 20 of the distal end surface further includes the first protective projection 62 and the second protective projection 64 in order to prevent a contacted member from coming into contact with the observation window 30. The first protective projection 62 is disposed on the side of the first illumination window 24 opposite to the observation window 30 on one side of the imaginary straight line 66 connecting the center of the observation window 30 and the center of the fluid jetting nozzle 28. Additionally, the second protective projection 64 is disposed on the side of the second illumination window 25 opposite to the observation window 30 on the other side of the imaginary straight line 66. That is, the first illumination window 24 is disposed between the observation window 30 and the first protective projection 62, and the second illumination window 25 is disposed between the observation window 30 and the second protective projection 64.

In the distal end surface illustrated in FIGS. 2 and 3, the first protective projection 62 is provided along the outer edge of the first surface 20 at a position adjacent to the first illumination window 24. Additionally, the first protective projection 62 is disposed in a shape cut out an outer periphery of the first illumination window 24. In an upper endoscope, in order to alleviate a burden on a patient at the time of inserting the endoscope 1, the reduction in diameter or size of the insertion part is required. Hence, since the positions of members to be disposed on the distal end surface are limited, there is a case where a space may not be sufficiently secured between the first illumination window 24 and the outer edge of the first surface 20. In the present embodiment, the first protective projection 62 can be disposed without enlarging the distal end part by adopting the cut-out shape.

Since the first protective projection 62 and the second protective projection 64 project toward the front side, in order not to damage the inside of a body cavity in a case where the insertion part 2 of the endoscope 1 is inserted into the subject, it is preferable that the first protective projection 62 and the second protective projection 64 have thicknesses in a planar direction and have distal ends formed into curved surfaces.

Additionally, by increasing the lengths of the first protective projection 62 and the second protective projection 64 in a length direction along the first surface 20 (a direction perpendicular to the longitudinal axis of the insertion part 2), the areas on the front side of the first protective projection 62 and the second protective projection 64 can be increased. By increasing the areas on the front side of the first protective projection 62 and the second protective projection 64, the area of contact with an affected area can be increased, and a force applied to the affected area in a case where the endoscope is inserted can be decentralized.

In addition, in FIGS. 2 and 3, although the first protective projection 62 is disposed along the first illumination window 24, the second protective projection 64 may be disposed along the second illumination window 25.

The extending part 32 is provided in the projecting part 22 so as to extend from the observation window 30 toward a side opposite to the fluid jetting nozzle 28. With respect to the contact of the distal end surface with the contacted member from the front side, the extending part 32 can be combined with at least one of the fluid jetting nozzle 28, the first protective projection 62, or the second protective projection 64, thereby preventing the contacted member from coming into contact with the observation window 30.

Figure 5:
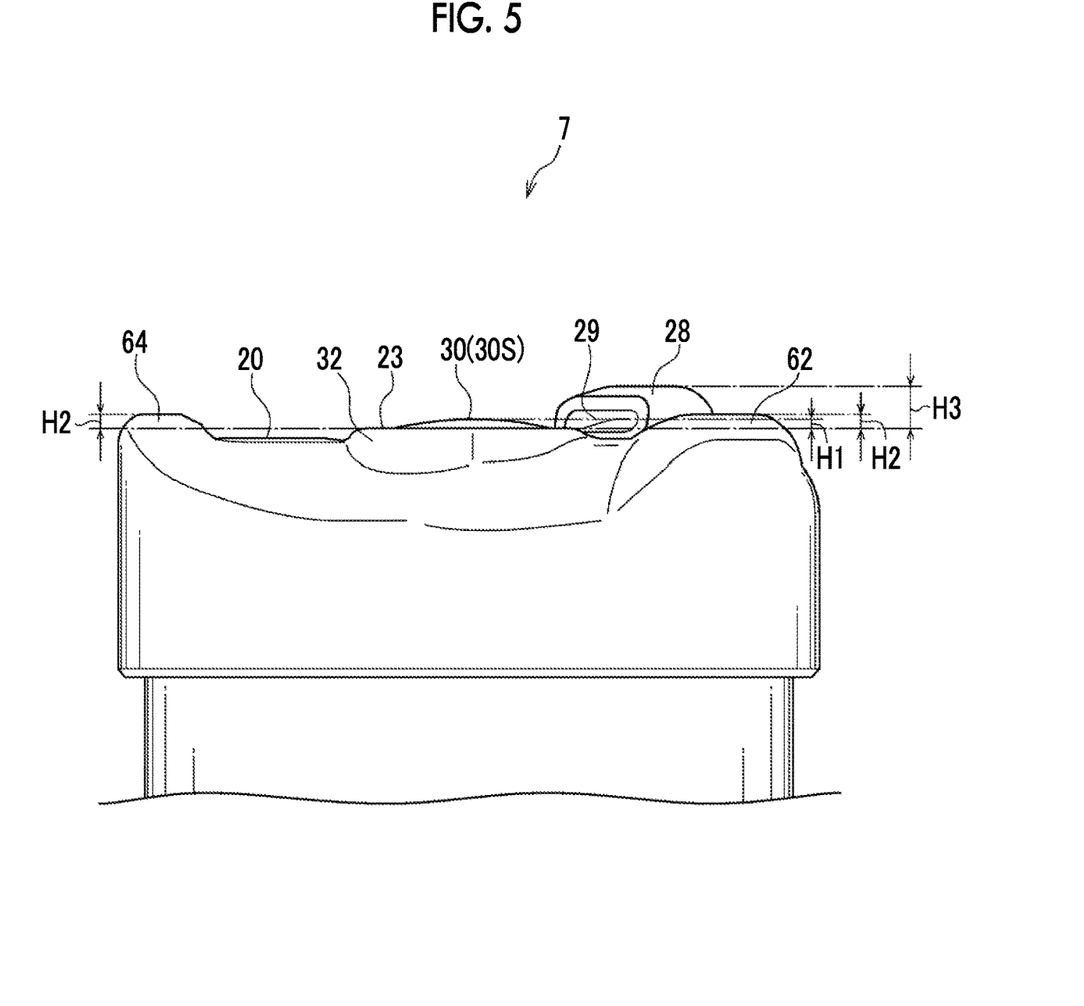
FIG. 5 is a side view of the distal end surface of FIG. 3 as seen from direction A.
Figure 6:
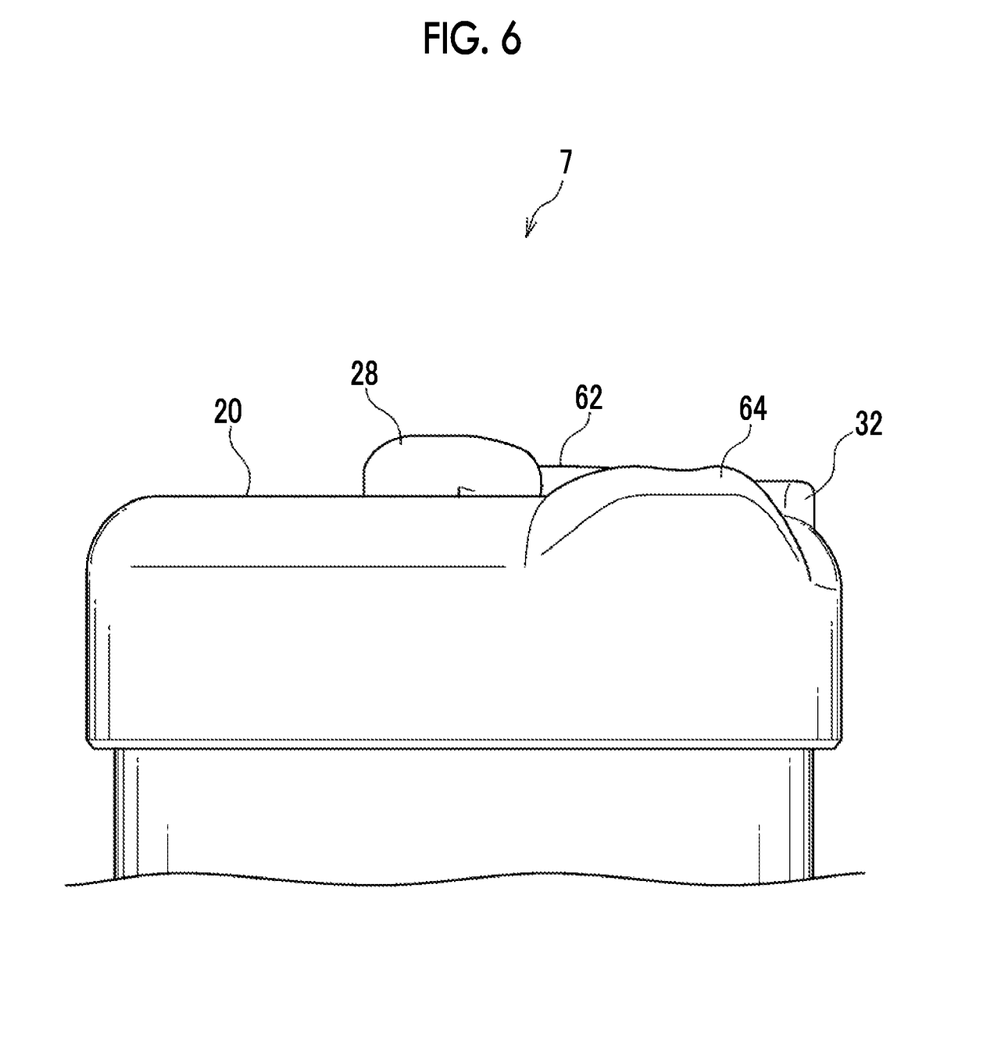
FIG. 6 is a side view of the distal end surface of FIG. 3 as seen from direction B.

Next, the height of the first protective projection 62 and the second protective projection 64 will be described with reference to FIGS. 5 and 6. FIG. 5 is a view as seen from arrow A in FIG. 3, and FIG. 6 is a view as seen from arrow B in FIG. 3.

In FIG. 5, in the heights of the distal end surface, a height up to the peak of the surface 30S of the observation window 30 in a case where the position of the second surface 23 (projecting part 22) is set as a reference position is indicated as H1, a height to the first protective projection 62 and the second protective projection 64 is indicated as H2, and a height up to the fluid jetting nozzle 28 is indicated as H3. Here, the "heights" mean distances (distances in the direction of the longitudinal axis of the insertion part 2) up to a reference surface in respective parts (the surface 30S of the observation window 30, the first protective projection 62, the second protective projection 64, and the fluid jetting nozzle 28) in a case where the second surface 23 is set as the reference surface. As illustrated in FIG. 5, the height H2 of the first protective projection 62 and the second protective projection 64 is set to be higher to the front side than the height H1 of the surface 30S of the observation window 30, and projects to the front side. Additionally, the height H3 of the fluid jetting nozzle 28 is set to be higher to the front side than the height H2 of the first protective projection 62 and the second protective projection 64, and the fluid jetting nozzle 28 is provided to project forward of the first protective projection 62 and the second protective projection 64. Additionally, the surface 30S of the observation window 30 is disposed forward of the extending part 32.

Additionally, a relationship between the heights of the extending part 32 and the observation window 30 is such that the observation window 30 is disposed at a position higher than (forward of) the extending part 32. This is to make it easier to remove the cleaning liquid jetted from the fluid jetting nozzle 28 toward the observation window 30.

It is preferable that the fluid jetting nozzle 28 is disposed forward of the first protective projection 62 and the second protective projection 64. Since the observation window 30 is provided forward of the extending part 32, the height on the front side of the fluid jetting nozzle 28 is increased. Accordingly, the position of the contacted member can be disposed forward of the observation window 30 in a case where the fluid jetting nozzle 28 and the extending part 32 come into contact with the contacted member. Thus, the contacted member coming into contact with the observation window 30 can be prevented.

Similarly, the first protective projection 62 and the second protective projection 64 are provided to project forward of the observation window 30. By providing the first protective projection 62 and the second protective projection 64 so a to project forward of the observation window 30, the first protective projection 62 and the second protective projection 64 can come into contact with the contacted member to prevent contact with the observation window 30.

In addition, in FIGS. 5 and 6, the front sides of the first protective projection 62 and the second protective projection 64 are formed as surfaces parallel to the first surface 20. However, the surfaces on the front sides of the first protective projection 62 and the second protective projection 64 can be formed obliquely toward the extending part 32 side. By adopting such a configuration, in a case where the contacted member comes into contact with the extending part 32, the first protective projection 62, and the second protective projection 64, the contacted member can be brought into linear contact or surface contact with the first protective projection 62 and the second protective projection 64.

In the present embodiment, in all combinations of imaginary planes capable of coming into contact with, from the front side, at least two of the fluid jetting nozzle 28, the first protective projection 62, and the second protective projection 64 that are formed on the first surface 20 and provided to project toward the front side of the observation window 30 and the extending part 32 provided to extend from the projecting part 22, the heights and the positions of the respective members are set such that the imaginary planes are disposed forward of the observation window 30. The positions of the distal end surface that comes into contact with the imaginary planes will be described with reference to FIGS. 7 to 9.

Figure 7:
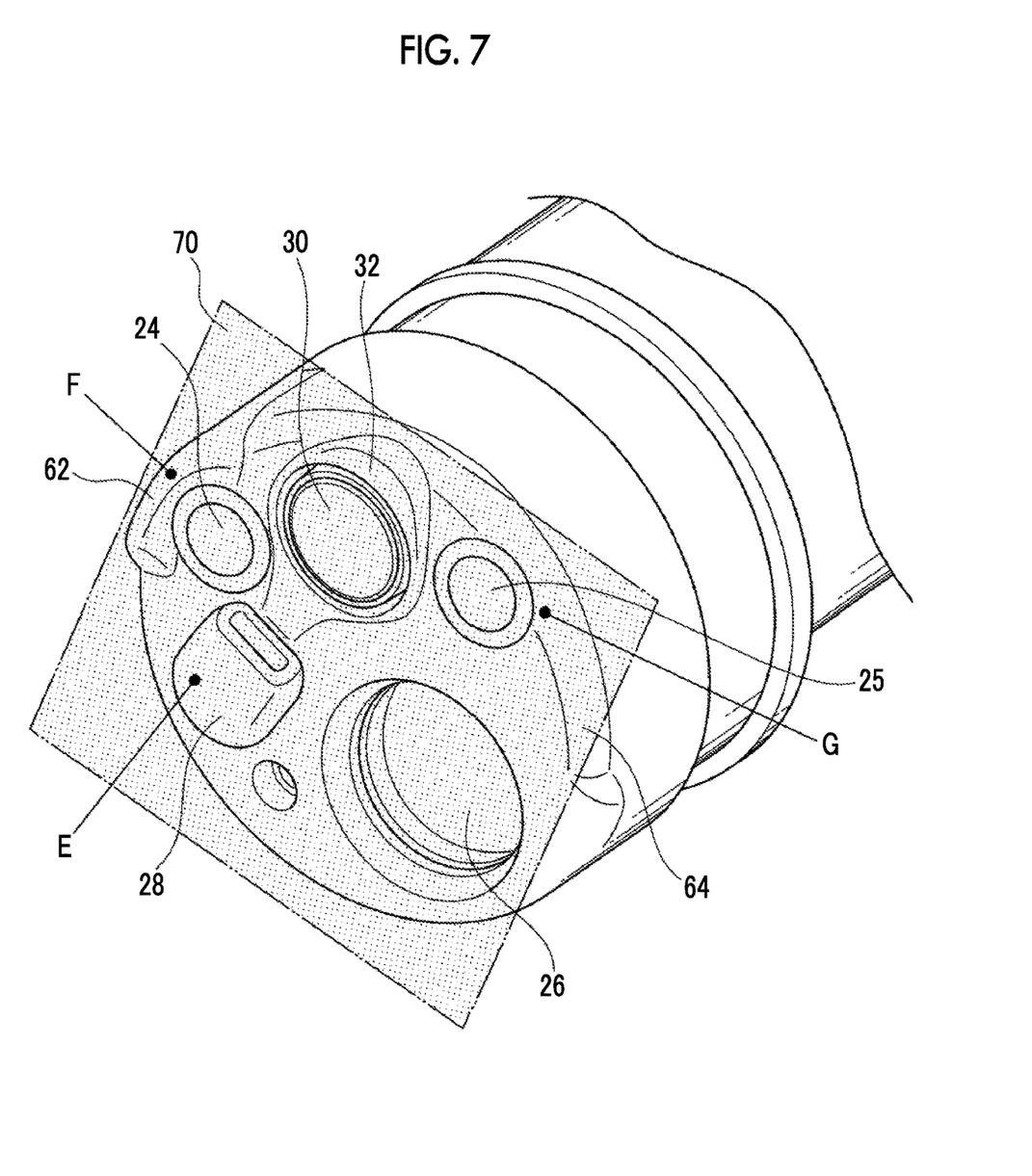
FIG. 7 is a view illustrating an example of an imaginary plane contacting the distal end surface.
Figure 8:
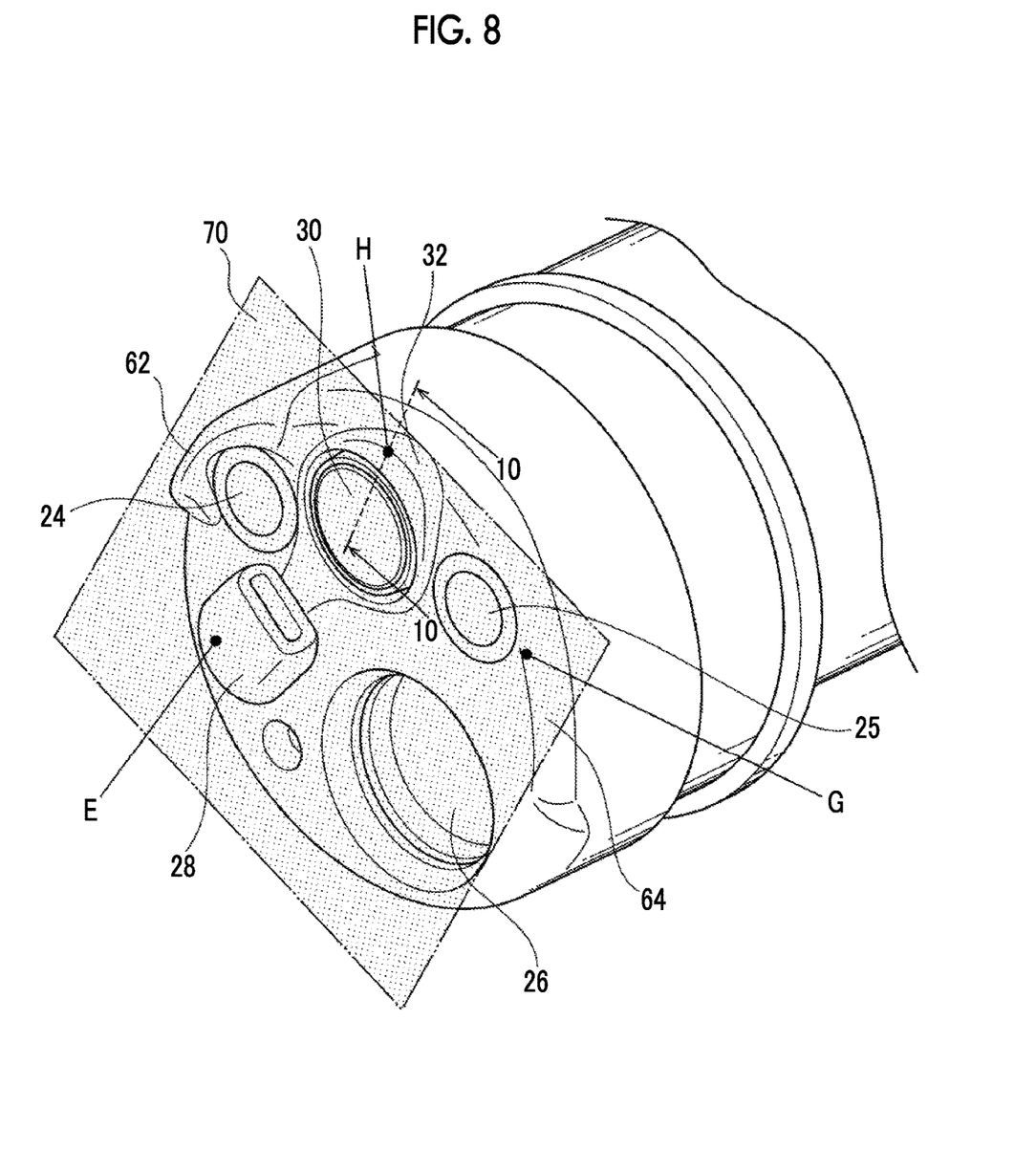
FIG. 8 is a view illustrating another example of the imaginary plane contacting the distal end surface.
Figure 9:
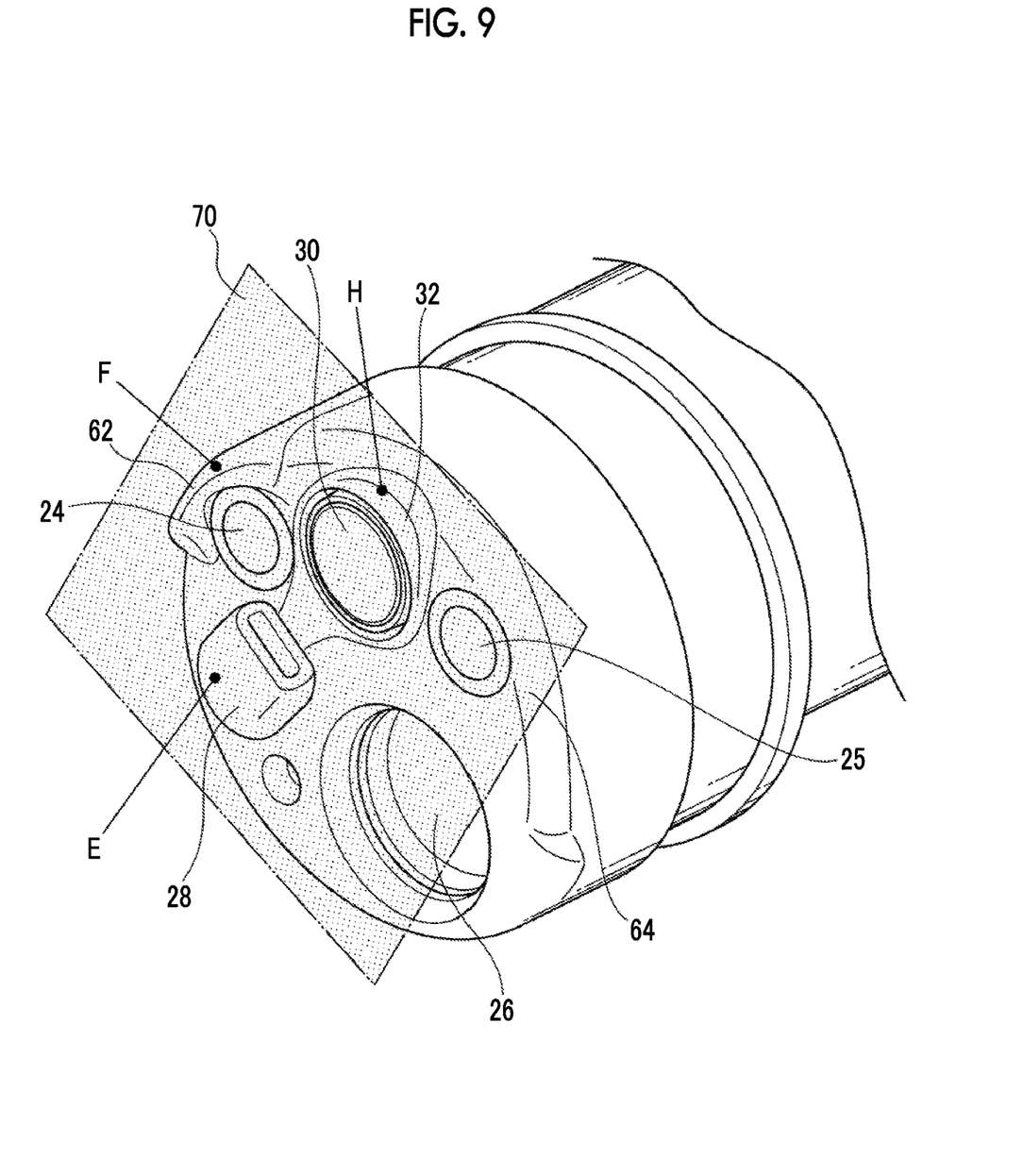
FIG. 9 is a view illustrating still another example of the imaginary plane contacting the distal end surface.

By disposing an imaginary plane 70 that comes into contact with the fluid jetting nozzle 28, the first protective projection 62, the second protective projection 64, and the extending part 32 in respective conditions illustrated in FIGS. 7 to 9, forward of the observation window 30, the contacted member can be prevented from coming into contact with the observation window 30 from the front side. As a first condition, FIG. 7 is a view illustrating a state where the imaginary plane 70 comes into contact with three points of the fluid jetting nozzle 28 (point E in the drawing), the first protective projection 62 (point F in the drawing), and the second protective projection 64 (point G in the drawing). As a second condition, FIG. 8 is a view illustrating a state where the imaginary plane 70 comes into contact with three points of the fluid jetting nozzle 28, the second protective projection 64, and the extending part 32 (point H in the drawing). As a third condition, FIG. 9 is a view illustrating a state where the imaginary plane 70 comes into contact with three points of the fluid jetting nozzle 28, the first protective projection 62, and the extending part 32.

The positions and the heights of the fluid jetting nozzle 28, the first protective projection 62, the second protective projection 64, and the extending part 32 are determined so as to satisfy all the first condition, the second condition, and the third condition. Specifically, the positions and the heights are determined by (1) changing the height of at least any one of the first protective projection 62 and the second protective projection 64, (2) changing the height of the fluid jetting nozzle 28, and (3) changing the length of the extending part. Additionally the invention is not limited to, and a planar positional relationship (distances) of the respective members may be changed. However, in a case where the endoscope of the present embodiment is the upper endoscope and the request for reduction in size of the distal end part is taken into consideration, an aspect in which (1) the height of the first protective projection 62 and the second protective projection 64 or (2) the height of the fluid jetting nozzle 28 is changed is preferable.

In addition, the surface 30S of the observation window 30 may be lowered from the distal end surface to a proximal end side, and may be adjusted so as to prevent contact with the imaginary plane 70.

Additionally, since the first illumination window 24 and the second illumination window 25 are provided adjacent to the first protective projection 62 and the second protective projection 64, the first illumination window 24 and the second illumination window 25, which are provided on the first surface 20 lower than the observation window 30, can also be prevented from coming into contact with the imaginary plane 70.

Figure 10:
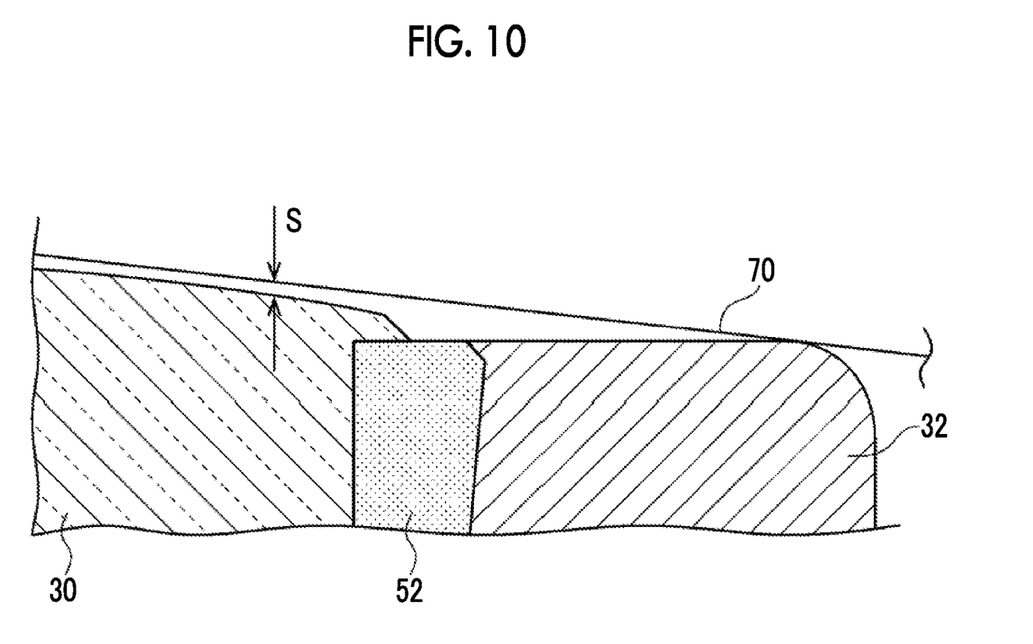
FIG. 10 is a sectional view as seen in the direction of arrow 10-10 of the distal end surface of FIG. 8.

FIG. 10 is a sectional view as seen in the direction of arrow 10-10 of the distal end part 7 in FIG. 8, and illustrates a positional relationship between the observation window 30 and the imaginary plane 70. A gap S can be provided by the extending part 32 and the imaginary plane 70 coming into contact with the fluid jetting nozzle 28 and the extending part 32. By providing the gap S, contact between the contacted member (imaginary plane 70) and the observation window 30 can be prevented. Hence, with respect to the contacted member coming into contact from the front side, the observation window 30 does not come into contact with the contacted member. Thus, damage to the observation window 30 can be prevented. Additionally, as described above, the observation window 30 is joined to the distal end part body 40 with the adhesive. By preventing the observation window 30 from coming into contact with the contacted member, peeling of the observation window 30 resulting from the contact can be prevented.

Figure 11:
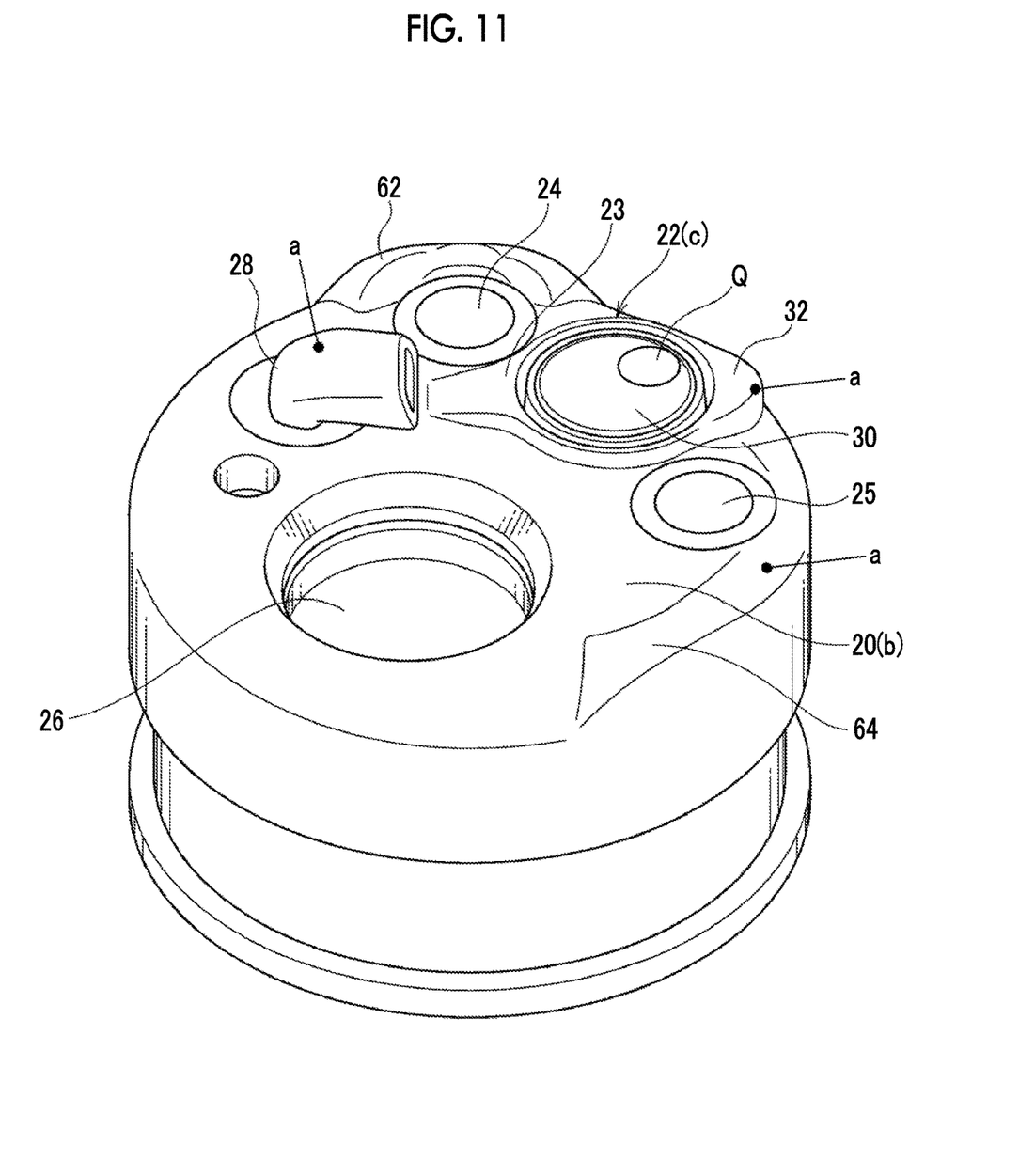
FIG. 11 is a view illustrating a condition under which the imaginary plane is disposed on a front side.

FIG. 11 is a view illustrating specific conditions that satisfy the above first to third conditions.

In a case where the first surface 20 is set as a reference surface (b), the height of the projecting part 22 on which the second surface 23 is formed is 0.2±0.02 (projecting part reference surface: c) (cm) from the reference surface (b). Additionally, the height of the fluid jetting nozzle 28 is 0.84 (cm) from the reference surface (b), and the height of the first protective projection 62 and the second protective projection 64 is c+0.22±0.02 (cm) from the projecting part reference surface (c). Additionally, the peak of a convex part of the observation window 30 is set to have c+0.15 (+0.02 to −0.05) (cm).

In a case where an imaginary plane coming into contact from the front side, and the imaginary plane comes into contact with the fluid jetting nozzle 28 and the extending part 32, the imaginary plane is inclined toward the extending part 32, and therefore, comes closest to an area Q of the observation window 30. Additionally, since the distance from the first protective projection 62 is such that the second protective projection 64 is disposed apart from the observation window 30, a case where the imaginary plane comes into contact with the second protective projection 64, that is, in FIG. 11, a case where the contact is made at three points of points a becomes a condition (the above second condition) under which the imaginary plane and the observation window 30 comes closest to each other. Hence, in a case where the imaginary plane is disposed forward of the observation window 30 under the second condition, it is considered that the imaginary plane is disposed forward of the observation window 30 even under the first and third conditions.

In a case where calculation is performed in the imaginary plane under the second condition, a gap 0.07 (+0.07 to −0.04) (cm) can be secured between the observation window 30 and the imaginary plane with respect to the imaginary plane from the front side. That is, 0.003 (cm) can be secured even at the narrowest position, and it can be confirmed that the contacted member from the front does not come into contact with the observation window 30.

In addition, in FIGS. 7 to 9, the imaginary plane 70 in which the imaginary plane 70 comes into contact with three points including the fluid jetting nozzle 28 has been described. However, a configuration in which the imaginary plane 70 coming into contact with three points of the first protective projection 62, the second protective projection 64 and the extending part 32 is disposed forward of the observation window 30 may be adopted. Additionally, a configuration in which an imaginary plane coming into contact with four points of the fluid jetting nozzle 28, the first protective projection 62, the second protective projection 64, and the extending part 32 is disposed forward of the observation window 30 may be adopted.

By adopting such a configuration, even in a case where the contacted member comes into contact with the distal end surface, the fluid jetting nozzle 28, the first protective projection 62, and the second protective projection 64 that project to the front side, and the extending part 32 extending from the projecting part 22 can prevent the contacted member from coming into contact with the observation window 30. Additionally, since the first illumination window 24 and the second illumination window 25 are disposed on the first surface 20 lower than the observation window 30, the fluid jetting nozzle 28, the first protective projection 62, the second protective projection 64, and the extending part 32 can prevent the illumination windows from coming into contact with the contacted member.

Here, the contacted member coming into contact with the observation window 30 can be prevented by making the first protective projection 62 and the second protective projection 64 project to the front side. However, in a case where the first and second projections excessively project to the front side, there is a case where the distal ends of the first protective projection 62 and the second protective projection 64 may be reflected within an endoscope observation visual field range to be observed in the observation window 30. Hence, it is preferable that the first protective projection 62 and the second protective projection 64 are disposed outside the endoscope observation visual field range. The endoscope observation visual field range is an image range within a monitor in a case where an observation image captured by the observation unit is output to the monitor (not illustrated) connected to the processor device. Moreover, it is preferable that the first protective projection 62 and the second protective projection 64 is disposed outside the visual field range of the observation window 30. The visual field range of the observation window 30 means a visual field range taken in via an optical system of the observation unit.

As for the extending part 32, It is preferable to design the distance from the observation window 30 to an outer end part of the extending part 32 such that the extending part 32 is disposed outside the endoscope observation visual field range to be observed in the observation window 30. Moreover, it is preferable to design the distance from the observation window 30 to the outer end part of the extending part 32 such that the extending part 32 is disposed outside the visual field range of the observation window 30. Additionally, in a case where the distance of an outer edge of the extending part 32 from the observation window 30 is increased, the outer edge of the extending part 32 projects from an outer edge of the distal end part body 40 in a plan view of the first surface 20 as seen from the front side. Thus, this is not preferable from a viewpoint of reduction in diameter of the distal end part.

EXPLANATION OF REFERENCES

1: endoscope
2: insertion part
3: operating part
4: universal cord
5: flexible part
6: bending part
7: distal end part
8, 9: angle knob
10: air/water supply button
11: suction button
12: treatment tool inlet
20: first surface
22: projecting part
23: second surface
24: first illumination window
24S, 25S, 30S, 52S, 58S, 60S: surface
25: second illumination window
26: treatment tool outlet
28: fluid jetting nozzle
28A: proximal end portion
28B: distal end portion
29: jetting nozzle
30: observation window
32: extending part
40: distal end part body
44: lens barrel
46: air/water supply channel
50, 54, 56, 61: opening
52: adhesive
62: first protective projection
64: second protective projection
66: imaginary straight line
70: imaginary plane

What is claimed is:

1. An endoscope comprising:
an insertion part to be inserted into a subject;
a first surface that constitutes a distal end surface of the insertion part;
a second surface that is formed on a projecting part projecting from the first surface to a front side;
an observation window that is provided on the second surface to observe an inside of the subject;
a nozzle that is provided on the first surface to jet a fluid toward the observation window;
a first protective projection that is provided on the first surface and is disposed on one side of an imaginary straight line connecting a center of the observation window and a center of the nozzle;
a second protective projection that is provided on the first surface and is disposed on the other side of the imaginary straight line;
a first illumination window that is provided on the first surface and is disposed between the observation window and the first protective projection; and
an extending part that is provided on the projecting part and extends from an edge of the observation window toward an outer edge of the first surface that is away from the nozzle,
wherein each of the nozzle, the first protective projection, and the second protective projection is projected distally from the observation window,
wherein the first protective projection and the second protective projection are in contact with and extended along the outer edge of the first surface.

2. The endoscope according to claim 1,
wherein the nozzle is provided to project forward of the first protective projection and the second protective projection.

3. The endoscope according to claim 1,
wherein the observation window is provided to project forward of the extending part.

4. The endoscope according to claim 2,
wherein the observation window is provided to project forward of the extending part.

5. The endoscope according to claim 1, further comprising:
a second illumination window that is provided on the first surface and is disposed between the observation window and the second protective projection.

6. The endoscope according to claim 2, further comprising:
a second illumination window that is provided on the first surface and is disposed between the observation window and the second protective projection.

7. The endoscope according to claim 3, further comprising:
a second illumination window that is provided on the first surface and is disposed between the observation window and the second protective projection.

8. The endoscope according to claim 5,
wherein at least one of the first protective projection or the second protective projection is disposed at a position adjacent to an illumination window disposed on the same side of the imaginary straight line.

9. The endoscope according to claim 1,
wherein the first protective projection and the second protective projection are disposed outside an endoscope observation visual field range.

10. The endoscope according to claim 9,
wherein the first protective projection and the second protective projection are disposed outside a visual field range of the observation window.
11. The endoscope according to claim 1,
wherein the extending part is disposed outside an endoscope observation visual field range.
12. The endoscope according to claim 11,
wherein the extending part is disposed outside a visual field range of the observation window.

\* \* \* \* \*